(12) United States Patent
Salzer

(10) Patent No.: US 7,438,796 B2
(45) Date of Patent: Oct. 21, 2008

(54) ELECTROCHEMICAL CHLORINE SENSOR

(75) Inventor: Corey A. Salzer, Fort Collins, CO (US)

(73) Assignee: Hach Company, Loveland, CO (US)

( * ) Notice: Subject to any disclaimer, the term of this patent is extended or adjusted under 35 U.S.C. 154(b) by 295 days.

(21) Appl. No.: 11/467,855

(22) Filed: Aug. 28, 2006

(65) Prior Publication Data
US 2008/0047846 A1    Feb. 28, 2008

(51) Int. Cl.
*G01N 27/413* (2006.01)
(52) U.S. Cl. ............. 205/778.5; 205/779.5; 204/400; 204/405
(58) Field of Classification Search ............. 204/400, 204/435; 205/778.5–779.5
See application file for complete search history.

(56) References Cited

U.S. PATENT DOCUMENTS

2005/0191429 A1    9/2005   Buck

OTHER PUBLICATIONS

Allen et al, J. Electroanalytical Chemistry, 178, 1984, pp. 69-86.*
Jiye Jin, et al., "A Miniaturized FIA System for the Determination of Residual Chlorine in Environmental Water Samples", Analytical Sciences, Jan. 2004, vol. 20, pp. 205-207.
E. Hugo Seymour, et al., "Reaction with N,N-Diethyl-p-phenylenediamine: A Procedure for the Sensitive Square-Wave Voltammetric Detection of Chlorine", Electroanalysis 15, No. 8 (2003), pp. 589-694.
Philip T. Radford, et al., "A Signal Amplification scheme for Ultrasensitive Amperometric Detection in Flowing Streams", Analytical Chemistry, vol. 71, No. 22, Nov. 15, 1999, pp. 5101-5108.
Abraham Ulman, "Formation and Structure of Self-Assembled Monolayers", Chem. Rev., 96, pp. 1533-1554 (1996).

* cited by examiner

*Primary Examiner*—Kaj K Olsen
(74) *Attorney, Agent, or Firm*—Samuel M. Freund; Cochran Freund & Young LLC

(57) ABSTRACT

A sensor for measurement of free chlorine and of total chlorine in aqueous solution including a working electrode having a self-assembled monolayer (SAM) formed on the surface thereof, producing a barrier which reduces the generation of background currents when electrical potentials are applied to the electrode, and blocks the reduction or oxidation of interfering species in the solution, is described. Such SAMs have also been found to block the efficient reduction of chlorine as well. However, N,N-diethyl-p-phenylenediamine (DPD) has been found to effectively transport electrons across the SAM; that is, an oxidized form of DPD produced by a reaction with chlorine is capable of penetrating the SAM such that the reduction of the oxidized DPD species can occur. The generated reduction current is correlated with the concentration of chlorine in solution. Total chlorine may be determined by the addition of an iodide salt.

28 Claims, 6 Drawing Sheets

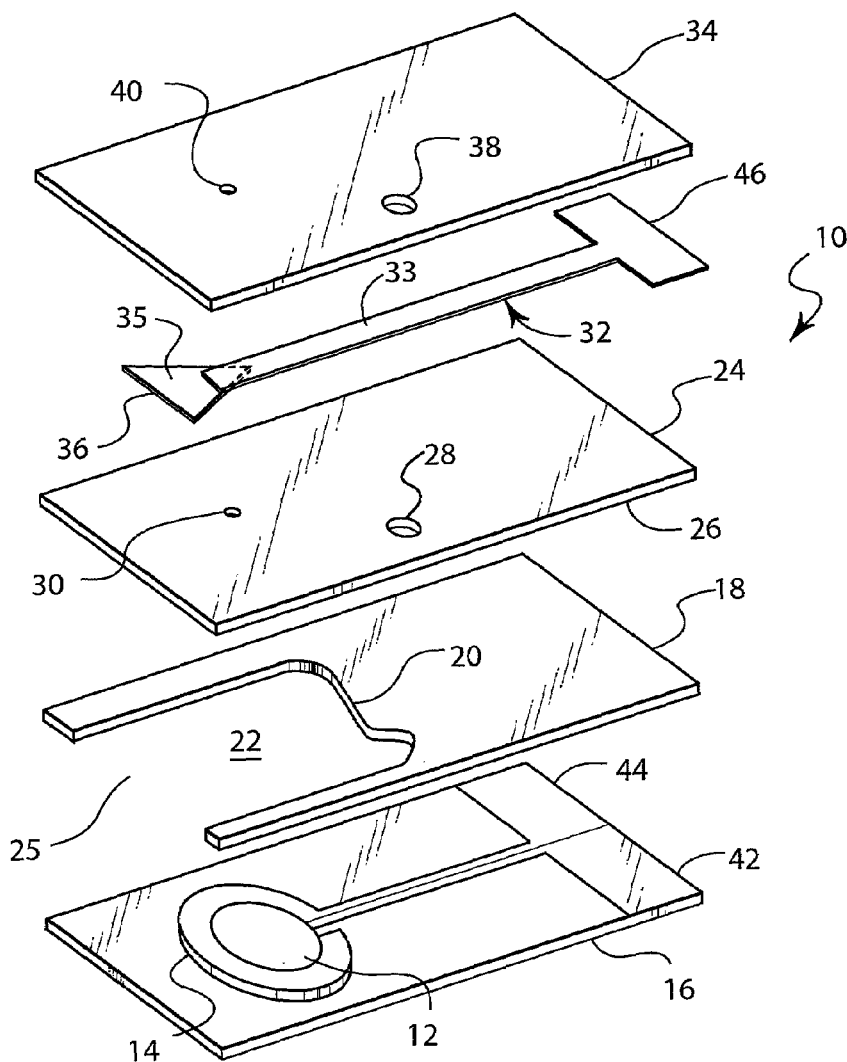
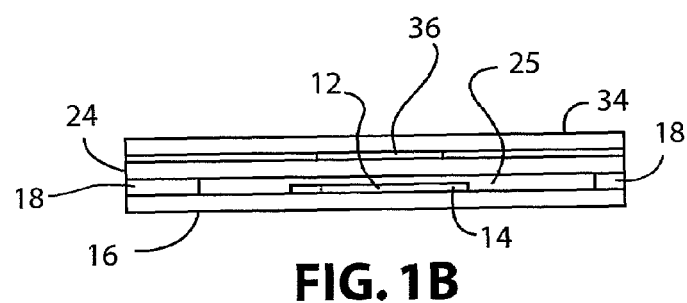

ELECTROCHEMICAL CHLORINE SENSOR

FIELD OF THE INVENTION

The present invention relates generally to chlorine analysis and, more particularly, to the electrochemical measurement of the concentration of free and total chlorine in water.

BACKGROUND OF THE INVENTION

Performance of small, inexpensive electrochemical sensors for rapid and accurate measurement of free and total chlorine in aqueous solution have been impacted by interfering background currents arising from changes in potential of the working electrode which defines the limit of detection for such devices ($\geqq 0.1$ ppm for chlorine). Such background currents may be measured in analyte-free solutions and subtracted from the current measured when analyte is present. However, the additional measurement increases the complexity of the sensor and increases the quantity of reagent required.

Flow-injection analysis allows the background current to decay to a minimum value under analyte-free conditions, at which time samples containing the analyte are injected into the background electrolyte solution and an amperometric signal is generated. Lower limits of detection of 5 ppb of chlorine have been reported using this detection method; however, controlled flow of fluids and analyte-free background solutions are required, making the system more complex. See, e.g., "A Miniaturized FIA System for the Determination of Residual Chlorine in Environmental Water Samples," by Jiye Jin et al., Anal. Sci. 20, pages 205-207 (2004).

Use of surrogate analytes for improving the selectivity of the electrochemical process has been reported. In "Reaction with N,N-Diethyl-p-phenylenediamine: A Procedure for the Sensitive Square-Wave Voltammetric Detection of Chlorine" by E. Hugo Seymour et al., Electroanalysis 15, pgs. 689-694 (2003), the authors reported the reaction of N,N-diethyl-p-phenylenediamine (DPD) with chlorine in solution which, when combined with square-wave voltammetry, was found to improve the sensitivity of chlorine measurements at a bare, glassy carbon electrode. The reaction was found to overcome problems related to the direct reduction of chlorine at the electrode surface, and provides selectivity for the determination of chlorine in the presence of other halogen species and sulfide. The technique yields a detection limit of 0.45 ppm for chlorine as $Cl_2$.

Self-assembled monolayers have been used for reduction of background and improving selectivity of electrochemical sensors. See, e.g., "A Signal Amplification Scheme for Ultrasensitive Amperometric Detection in Flowing Streams" by Phillip T. Radford et al., Anal. Chem. 71, pgs. 5101-5108 (1999), wherein the authors demonstrated that a self-assembled monolayer (SAM) formed on a gold electrode provides selective oxidation of a poorly hydrated and neutral ferrocene species over that of a strongly hydrated and charged ferrocyanide species.

Accordingly, it is an object of the present invention to provide an apparatus and method for rapidly measuring the concentrations of free chlorine and total chlorine in aqueous samples having low chlorine concentrations.

Another object of the present invention is to provide an apparatus and method for rapidly measuring the concentration of free chlorine and total chlorine in aqueous samples having low chlorine concentrations, and requiring small sample volumes.

Yet another object of the present invention is to provide an apparatus and method for rapidly measuring the concentration of free chlorine and total chlorine in aqueous samples having low chlorine concentrations, and requiring small reagent volumes.

Still another object of the present invention is to provide an apparatus and method for rapidly measuring the concentration of free chlorine and total chlorine in aqueous samples having low chlorine concentrations, and employing a single-use, disposable sensor.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention as embodied and broadly described herein, the method for measuring chlorine in an aqueous sample, hereof, includes the steps of: generating a self-assembled monolayer of a thiol on the surface of a gold working electrode; forming a buffered solution of a salt of N,N-diethyl-p-phenylenediamine and the sample; exposing the working electrode, an auxiliary electrode and a reference electrode to the solution; applying a chosen voltage between the working electrode and the reference electrode, whereby a current is generated between the working electrode and the auxiliary electrode; and measuring the current, whereby the free chlorine in the sample is determined therefrom.

In another aspect of the present invention, and in accordance with its objects and purposes, the method for measuring chlorine in an aqueous sample, hereof, includes the steps of: generating a self-assembled monolayer of a thiol on the surface of a gold working electrode; forming a buffered solution of a salt of N,N-diethyl-p-phenylenediamine, an iodide salt and the sample; exposing the working electrode, an auxiliary electrode and a reference electrode to the solution; applying a chosen voltage between the working electrode and the reference electrode, whereby a current is generated between the working electrode and the auxiliary electrode; and measuring the current, whereby the total chlorine in the sample is determined therefrom.

In yet another aspect of the present invention, and in accordance with its objects and purposes, the apparatus for measuring chlorine in an aqueous sample, hereof, includes in combination: a gold working electrode having a surface onto which a self-assembled monolayer of a thiol is formed; an auxiliary electrode; a reference electrode; means for exposing the working electrode, the auxiliary electrode and the reference electrode to a buffered solution of a salt of N,N-diethyl-p-phenylenediamine and the sample; means for applying a chosen voltage between the working electrode and the reference electrode producing thereby a current between the working electrode and the auxiliary electrode; and means for measuring the current, whereby the free chlorine in the sample is determined therefrom.

In still another aspect of the present invention, and in accordance with its objects and purposes, the apparatus for measuring chlorine in an aqueous sample, hereof, includes in combination: a gold working electrode having a surface onto which a self-assembled monolayer of a thiol is formed; an auxiliary electrode; a reference electrode; means for exposing the working electrode, the auxiliary electrode and the reference electrode to a buffered solution of a salt of N,N-diethyl-p-phenylenediamine, an iodide salt and the sample; means for applying a chosen voltage between the working electrode and the reference electrode producing thereby a current between the working electrode and the auxiliary electrode; and means for measuring the current, whereby the total chlorine in the sample is determined therefrom.

Benefits and advantages of the present invention include, but are not limited to, an apparatus and method for rapid, sensitive and accurate measurement of free and total chlorine in aqueous samples which requires only small quantities of test reagents and samples.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 1A is a schematic representation of an isometric exploded view of one embodiment of the chlorine sensor of the present invention, while FIG. 1B is a planar front view of the assembled chlorine sensor shown in FIG. 1A hereof.

FIG. 4A is a graph of the measured current as a function of the concentration of free chlorine in an aqueous solution using the apparatus illustrated in FIG. 3 hereof, while

DETAILED DESCRIPTION OF THE INVENTION

Figure 2:
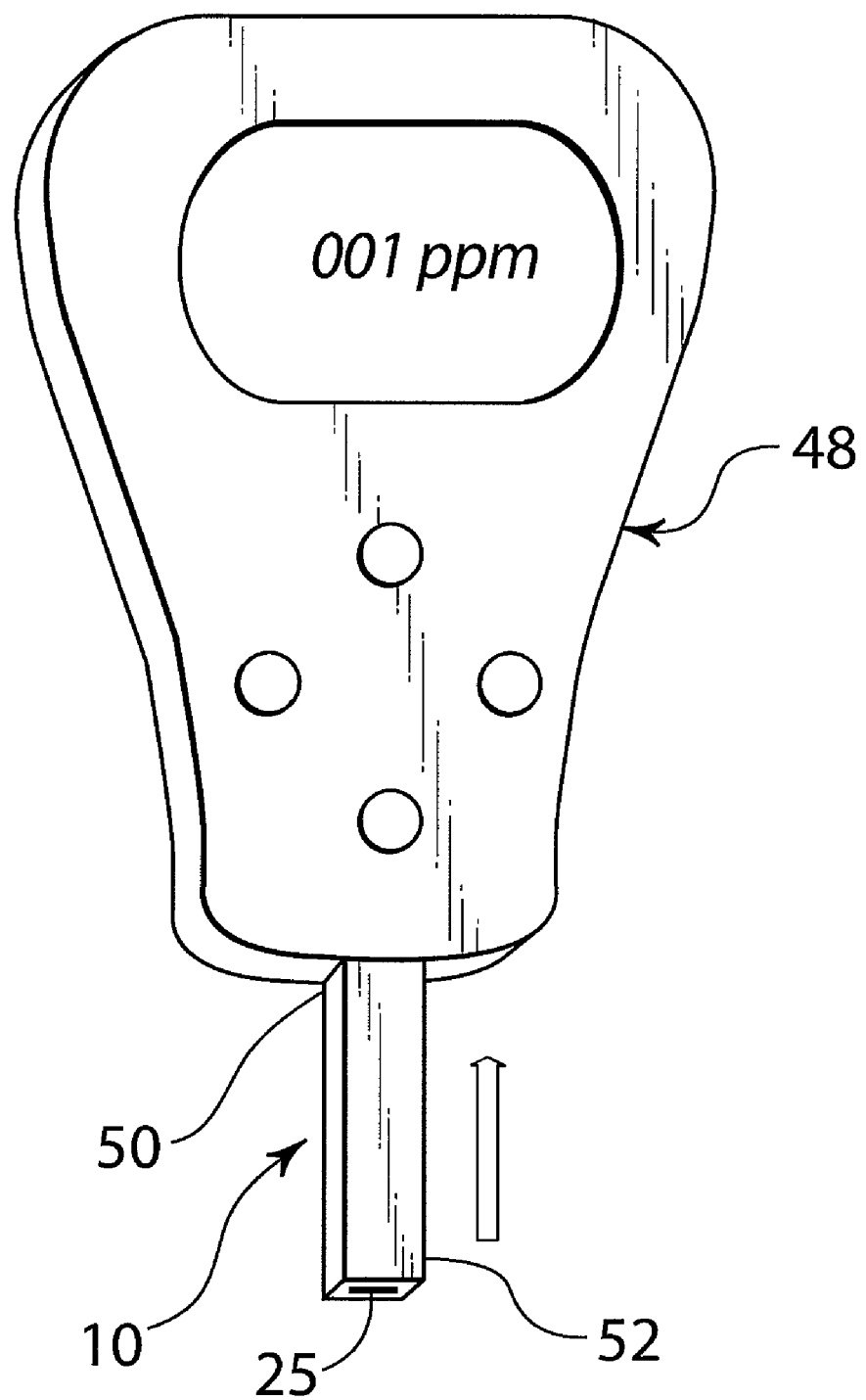
FIG. 2 is a schematic representation of an isometric view of the total chlorine and free chlorine measuring apparatus of the present invention showing the chlorine sensor illustrated in FIG. 1 hereof being in electrical communication with a measuring apparatus prior to contacting the sensor with a sample and commencing measurement of the chlorine concentration therein.

Briefly, the present invention includes a sensor for measuring free chlorine and total chlorine in aqueous solution comprising a working electrode having a self-assembled monolayer (SAM) formed on the surface thereof, producing a barrier which reduces the generation of background currents when electrical potentials are applied to the electrode, and blocks the reduction or oxidation of interfering species in the solution. Such SAMs have also been found to block the efficient reduction of chlorine as well. However, N,N-diethyl-p-phenylenediamine (DPD) has been found to effectively transport electrons across the SAM; that is, an oxidized form of DPD produced by a reaction with chlorine is capable of passing through or penetrating the SAM such that the reduction of the oxidized DPD species can occur. The generated reduction current is correlated with the concentration of free chlorine in solution. Total chlorine may be determined by the addition of an iodide salt.

Satisfactory performance has been found for those alkanethiols that have carbon chain-lengths $\geq$C6. Alkanethiols up to 1-octadecanethiol (C18) have been investigated by the present inventor. In the EXAMPLE hereinbelow, 1-dodecanethiol (C12) was employed. Other thiols, such as 11-mercapto-1-undecanol (having a polar alcohol terminus) or 3,3, 4,4,5,5,6,6,7,7,8,8,9,9,10,10,10-heptadecafluoro-1-decanethiol (a fluorinated thiol) have been tested and found to work as blocking layers as well. It is anticipated that many other thiols will work well; for example, in addition to other alkane thiols, thiols having an aromatic ring in the alkane chain and others having polymerizable groups in the chain that permits cross-linking between the molecules in the SAM.

The DPD employed in the EXAMPLE hereinbelow was a salt of N,N-diethyl-p-phenylenediamine, which may be an oxalate or sulfate, as examples, at concentrations between 1.0 and 5.0 percent (w/w) in the reagent/buffer mixture.

For measurement of the total chlorine in solution, KI, or other iodide, is added to the reagents in the solution; reaction of $I^-$ with free or combined chlorine forms iodine which oxidizes the DPD species, thereby generating a reduction current. Measurement of free chlorine includes the measurement of HOCl and OCl$^-$, whereas measurement of total chlorine includes the measurement of HOCl and OCl$^-$, plus combined chlorine, which includes $NH_2Cl$, $NHCl_2$, and $NCl_3$. Combined chlorine can be mathematically determined by subtraction of the free chlorine measurement from a total chlorine measurement from the same sample. It has been found that measurements of free chlorine can be performed in approximately 1 min. while those for total chlorine may be achieved in about 3 min. using the apparatus and method of the present invention. Current measurements can be performed in about 10 s; however, dissolution of reagents and buffer materials in the sample, and the reaction time of the DPD with the analyte are the rate determining steps.

Amperometric measurements were made using the working electrode by contacting this electrode, an auxiliary electrode and a reference electrode with the chlorine-containing solution to which DPD and buffers are added. Samples were buffered to pH values between 6.0 and 7.0 using phosphate salts, such as sodium phosphate, as an example. Disodium ethylenediaminetetraacetic acid was also added to the reagent mixture as a chelant. It is anticipated that between approximately 7 µg and 2 mg of reagent and buffer materials will be required for accurate chlorine measurements. A reference electrode is used to ensure proper control of the potential applied to the working electrode in samples of unknown and varying compositions; particularly with regard to salinity. This differs from biological electrochemical sensors; for example, for glucose, which utilize samples having known composition. An auxiliary electrode is used in the common three-electrode arrangement, to accept current from the working electrode. Generally, current is not passed between the reference electrode and the working electrode.

A computer-controlled potentiostat governs the electrode operations and records the currents for conversion to concentration values, as would be understood by one skilled in the art of electrochemistry. The potential applied to the working electrode in the sensor is controlled by the potentiostat with reference to the reference electrode on the sensor. Current is passed between the working electrode and the auxiliary electrode as needed to ensure the redox reaction at the working electrode proceeds unimpeded. The current generated at the working electrode is used to quantify the chlorine concentration in the sample. The potentiostat employed measures currents between $1 \times 10^{-9}$ A and $5 \times 10^{-6}$ A, but may also measure charge passed by integration of the measured current. The charge may also be correlated with the desired chlorine measurement. The potentiostat may be a handheld or bench top apparatus. The sensor is attached to electrical contacts on the potentiostat for use in measurement. Sensors may also be dispensed from a containment unit in or on the potentiostat such that they are placed into proper electrical communication for the measurement. Used sensors may be released from the potentiostat for disposal by a mechanical mechanism in the potentiostat so the user does not need to contact the sensor.

Reference will now be made in detail to the present preferred embodiments of the inventions, examples of which are illustrated in the accompanying drawings. In the Figures, similar or identical structure will be identified using identical callouts. Turning now to FIG. 1, a schematic representation of an isometric exploded view of one embodiment of chlorine sensor, 10, of the present invention is shown. Working electrode, 12, and auxiliary electrode, 14, are formed from a thin layer (for example, 50 nm) of gold deposited on polymer substrate, 16. This may be achieved by sputtering or vapor deposition, as examples. SAMs of thiols form readily on gold surfaces. See, e.g., "Formation and Structure of Self-Assembled Monolayers" by Abraham Ullman, Chem. Rev. 96, pgs. 1533-1554 (1996). Carbon auxilliary electrode may also be used.

Polymer spacer, 18, having cutout, 20, is placed over electrodes 12 and 14 to form volume, 22, (between approximately 1 μL and 200 μL in volume) effective for containing reagents and buffer materials. Polymer layer, 24, having hydrophilic layer, 26, facing void 22 is placed over spacer 18 such that with substrate 16, volume 22 is bounded and forms a capillary having opening, 25. Layer 24 has hole, 28, therein for permitting air to escape from void 22, and hole, 30, therein for permitting liquids in volume 22 to contact reference electrode, 32 (See, e.g., U.S. Patent Application Publication No. US2005/0191429 for Reference Electrode by Michael D. Buck, the teachings of which are hereby incorporated by reference herein, for an example of a suitable reference electrode.). Metal/metal salt layer, 33, of reference electrode 32 is formed on polymer substrate, 34, with alkali metal salt layer, 35, overlapping layer 33 in the region of hole 30 in layer 24, the two layers being sandwiched between substrate 34 and layer 24. Edge, 36, of metal salt layer 35 may contact the aqueous sample when sensor 10 is employed, and liquid enters reference electrode 32 by capillary action between substrate 34 and layer 24. It is generally undesirable for the reference electrode to be exposed to the buffered solution containing DPD and the iodide salt, if present, in volume 22; therefore, hole 30 provides an ion path between reference electrode 32 and electrodes 12 and 14 in volume 22, and reference electrode 32 is exposed directly to the sample through edge 36. Holes, 38 and 40, in substrate 34 are aligned with holes 28 and 30 in layer 24, respectively. Electrical contact pads, 42, 44 and 46, permit electrical connection to be made between chlorine sensor 10 and an electrical measurement apparatus.

FIG. 2 is a schematic representation of an isometric view of the total chlorine and free chlorine measuring apparatus, 48, of the present invention showing end, 50, of chlorine sensor 10 bearing electrical contacts 42, 44 and 46, illustrated in FIG. 1 hereof, being plugged into measuring apparatus 48 such that end, 52, thereof having capillary opening 25 is exposed prior to contact with the sample and the commencement of the measurement of the chlorine concentration therein. Sample is introduced into sensor 10 by contacting end 52 of the sensor to the sample, and permitting several seconds to elapse for sample to be drawn into capillary opening 25 and into reference electrode 32. Reagents and buffer materials already disposed in void 22 dissolve in the sample liquid to a chosen concentration, and react with the chlorine-containing species therein.

After a chosen time period, an electric potential is applied to working electrode 12, as described hereinabove. The oxidized DPD is reduced and a current is generated in response thereto which may be correlated to the concentration of chlorine analyte to be determined. After measurement, sensor 10 may be removed or ejected from measurement apparatus 48 and disposed of.

Having generally described the present method, more details thereof are presented in the following EXAMPLE.

EXAMPLE

Figure 3:
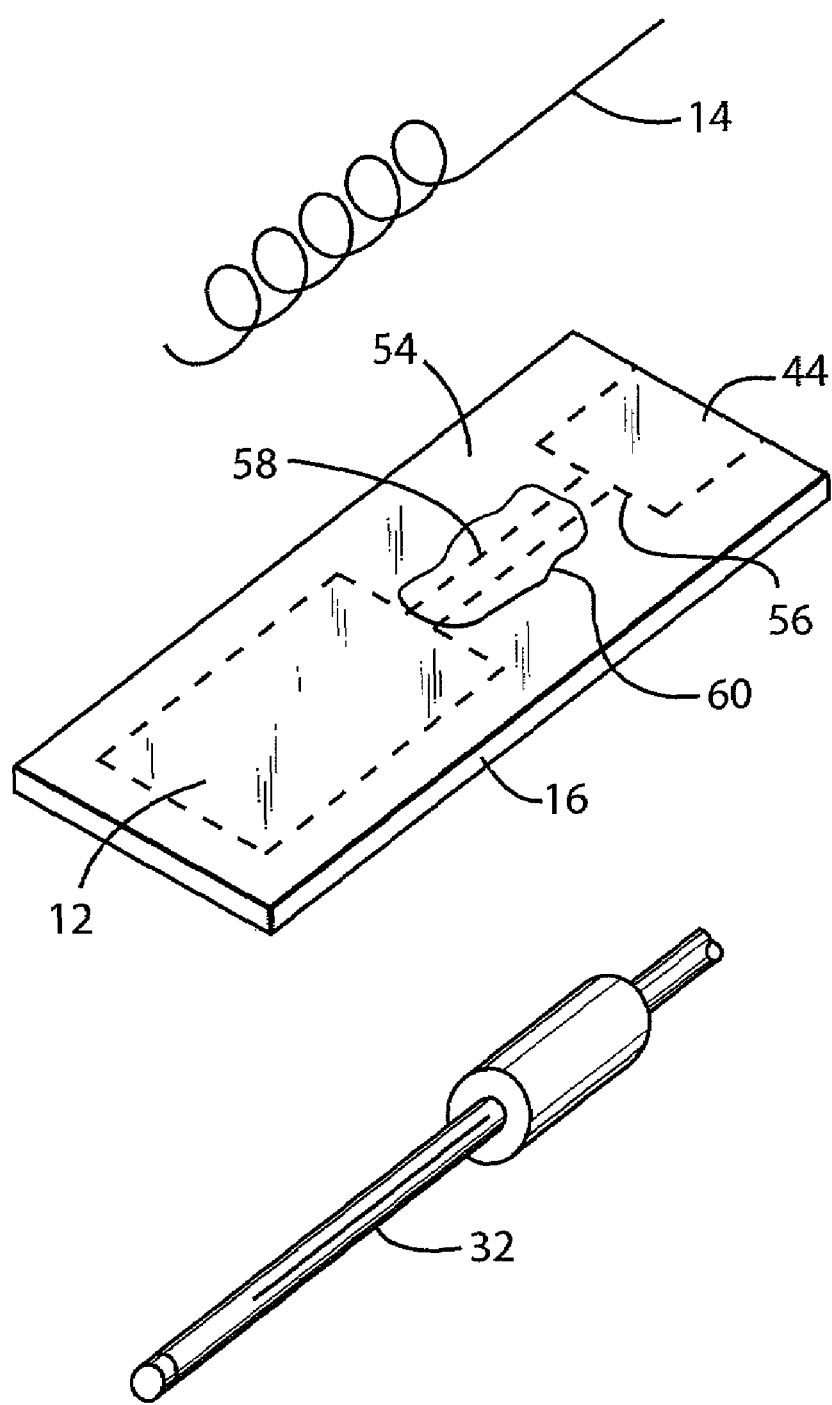
FIG. 3 is a schematic representation of an isometric exploded view of the chlorine sensor hereof used to obtain the data presented in FIGS. 4A, 4B and 5, hereof.

The apparatus used for testing the method of the present invention is illustrated in FIG. 3 hereof. Gold surface, 54, was formed on insulating polymer substrate 16, and shaped using laser etching (dashed line, 56), to form working electrode 12, contact pad 44, and connecting portion, 58. After laser forming, the electrodes were washed using deionized water and ethanol and placed in a dilute (~8 mM) thiol solution in ethanol for 24 h to permit formation of the SAM thereon, after which they were rinsed with deionized water and allowed to air dry. Dielectric enamel, 60, was used for masking region 58 of the electrodes such that it is not exposed to samples. External silver/silver chloride reference electrode 32 was used to ensure proper control of the potential applied to working electrode 12 in samples having unknown and varying compositions, particularly with regard to salinity. This differs from biological electrochemical sensors, such as those used for glucose measurement, which utilize a sample of relatively known composition. A platinum wire was employed as auxiliary electrode 14.

Samples were placed in a vessel (not shown in FIG. 3) along with reagents and buffers before measurements were made. The three electrodes (12, 14 and 32) were connected to a measuring apparatus (also not shown in FIG. 3), and measurements were taken.

Figure 4A:
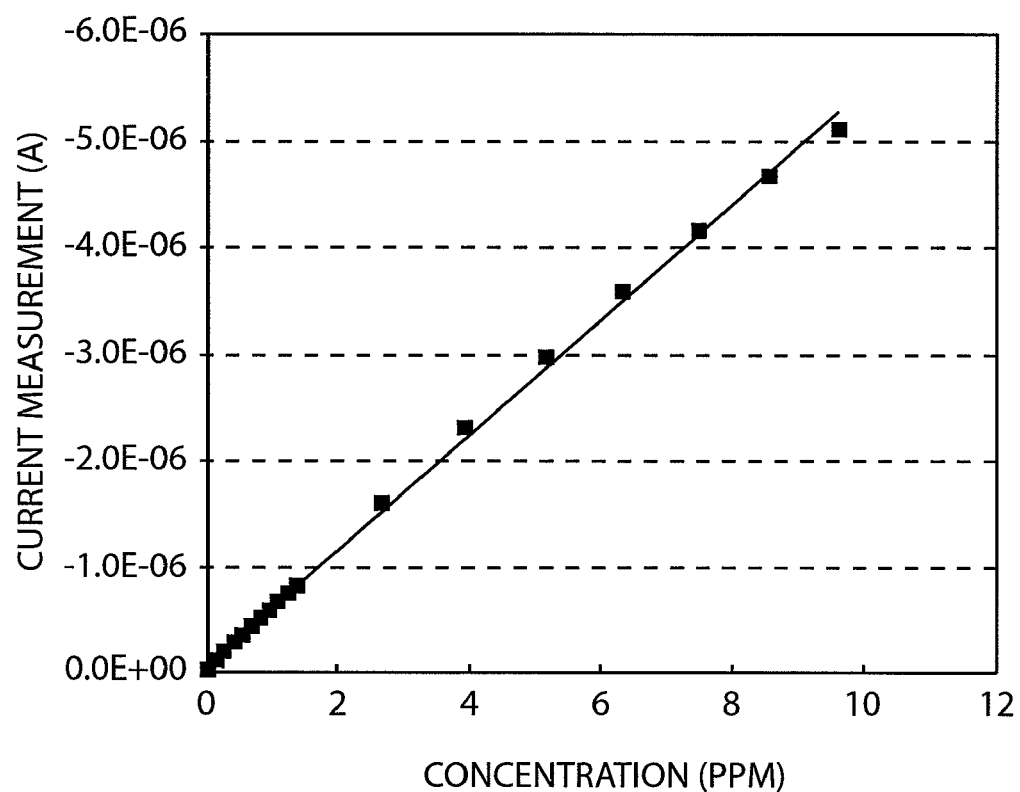
Figure 4B:
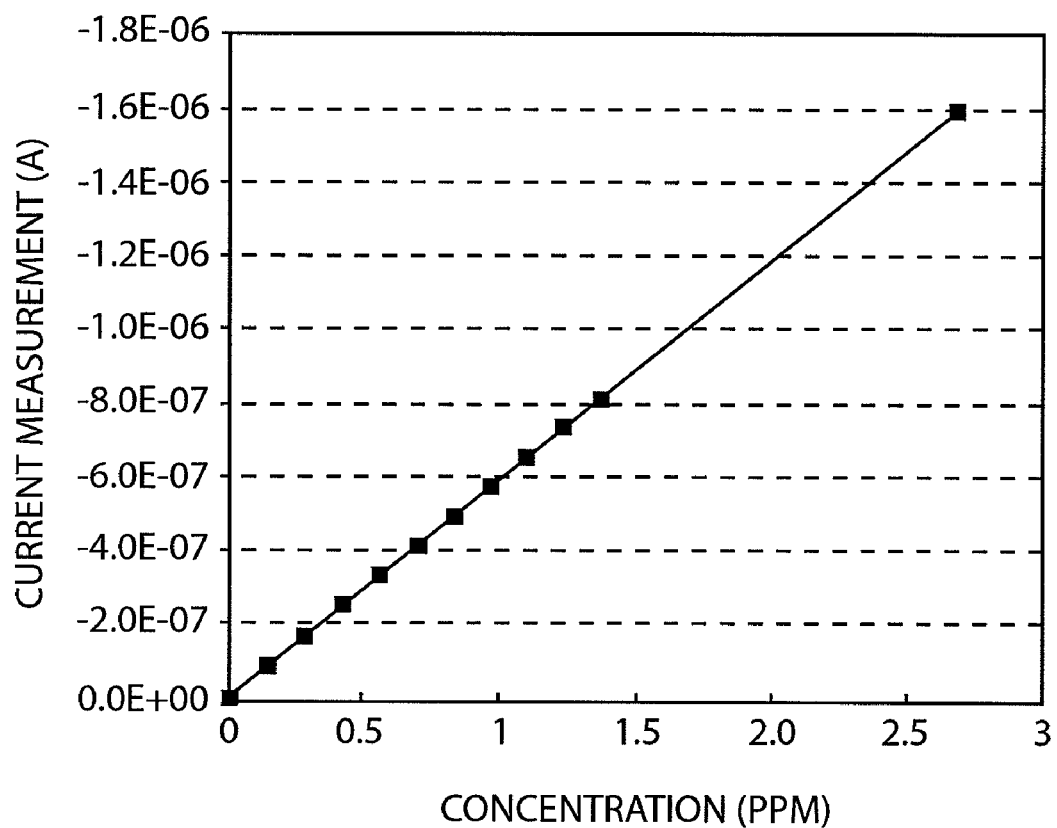
FIG. 4B is a graph of the measured current as a function of the concentration of free chlorine in an aqueous solution for lower chlorine concentrations, using the apparatus illustrated in FIG. 3 hereof.

FIG. 4A is a graph of the measured current as a function of the concentration of free chlorine in an aqueous solution using the apparatus illustrated in FIG. 3 hereof, while FIG. 4B is a graph of the measured current as a function of the concentration of free chlorine in an aqueous solution for lower concentrations of chlorine, using the apparatus illustrated in FIG. 3 hereof.

Figure 5:
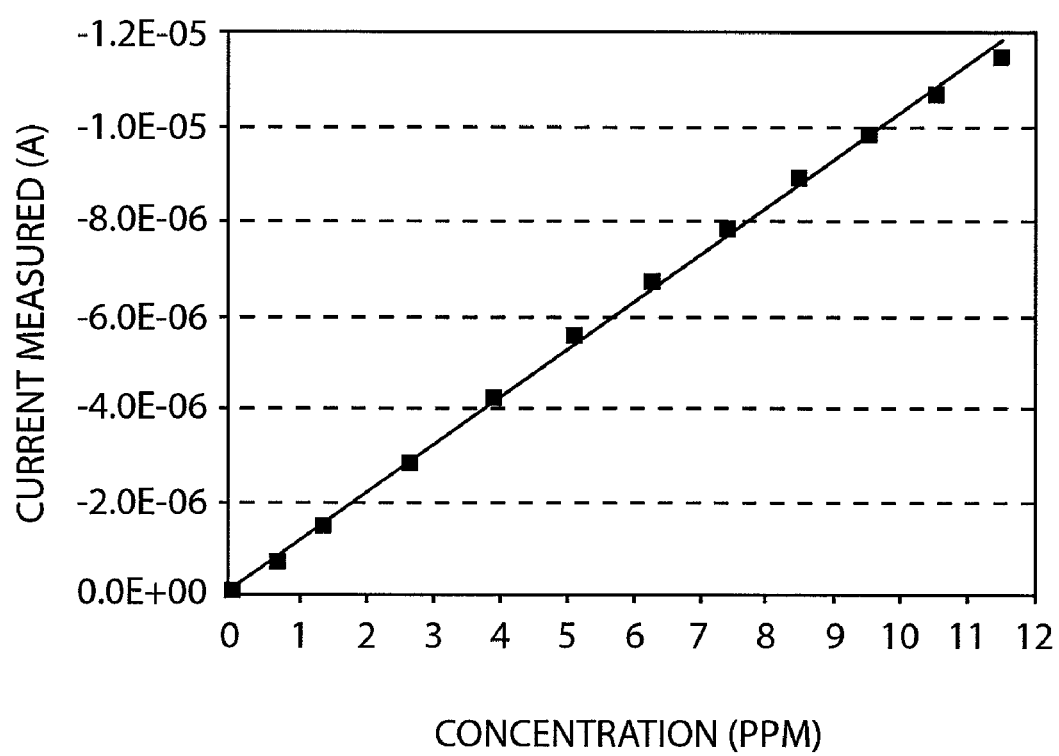
FIG. 5 is a graph of the measured current as a function of total chlorine in an aqueous solution using the apparatus illustrated in FIG. 3 hereof.

FIG. 5 is a graph of the measured current as a function of total chlorine in an aqueous solution using the apparatus illustrated in FIG. 3 hereof.

The present sensor shows linearity between 0 and 10 ppm of $Cl_2$ for both free and total chlorine. The upper limit appears to be dictated by the chemistry between DPD and chlorine. The limit of detection has been calculated to be approximately 20 ppb as $Cl_2$, with a measurement precision of about ±15 ppb. Chlorine measurements are not observed to be impacted by interferences such as common iron and copper salts, or by hardness or alkalinity, to levels acceptable by current DPD-based calorimetric methods.

Temperature has been found to influence the sensitivity of the present apparatus; therefore, temperature compensation may be required. Further, lack of sample quiescence once drawn into the sensor has been found to adversely affect the measurement. Small capillaries have been found to perform better than larger capillaries.

For measurement of total chlorine, it was found that DPD was not required, as the iodine formed in the reaction between the potassium iodide reagent and the chlorine in solution could be reduced at the SAM-coated working electrode. However loss of iodine to the sensor makes lower concentrations difficult to accurately measure. Addition of DPD minimizes the halogen uptake losses, thereby preserving the analytical signal. Comparison of background currents generated by gold electrodes with and without the SAM coating have shown more than an order of magnitude decrease in the background current for the SAM-treated electrode of FIG. 3 hereof ($2.7 \times 10^{-7}$ A, versus $4.9 \times 10^{-9}$ A). Changing the concentration or type of electrolyte or buffer in solution was found to have little impact on this effect.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for measuring chlorine in an aqueous sample, comprising the steps of:
    forming a self-assembled monolayer of a thiol on the surface of a gold working electrode;
    forming a buffered solution of a salt of N,N-diethyl-p-phenylenediamine and the sample;
    exposing the working electrode, an auxiliary electrode and a reference electrode to the solution;
    applying a chosen voltage between the working electrode and the reference electrode, whereby a current is generated between the working electrode and the auxiliary electrode; and
    measuring the current, whereby the free chlorine in the sample is determined therefrom.

2. The method of claim 1, further comprising the step of adding an iodide salt to the buffered solution, whereby the total chlorine in the sample is determined.

3. The method of claim 2, wherein the iodide comprises alkaline iodide.

4. The method of claim 3, wherein the alkaline iodide comprises potassium iodide.

5. The method of claim 2, further comprising the step of determining the combined chlorine concentration in the sample by subtracting the free chlorine measurement from the total chlorine measurement.

6. The method of claim 1, wherein the solution is buffered at a pH between 6 and 7.

7. The method of claim 6, wherein the solution is buffered using phosphate salts.

8. The method of claim 6, wherein disodium ethylenediaminetetraacetic acid is added to the solution.

9. The method of claim 1, wherein the auxiliary electrode is selected from the group consisting of gold electrodes and carbon electrodes.

10. The method of claim 1, wherein the salt of N,N-diethyl-p-phenylenediamine is selected from the group consisting of oxalates and sulfates.

11. The method of claim 1, wherein the thiol is selected from the group consisting of alkanethiols, thiols having an alcohol terminus, and fluorinated thiols.

12. The method of claim 11, wherein the alkanethiols comprise alkanethiols having a carbon chain length greater than or equal to six carbon atoms.

13. The method of claim 12, wherein the alkanethiol comprises 1-dodecanethiol.

14. The method of claim 11, wherein the thiol having an alcohol terminus comprises 11-mercapto-1-undecanol, and the fluorinated thiols comprise 3,3,4,4,5,5,6,6,7,7,8,8,9,9,10,10,10-heptadecafluoro-1-decanethiol.

15. An apparatus for measuring chlorine in an aqueous sample, comprising in combination:
    a gold working electrode having a surface onto which a self-assembled monolayer of a thiol is formed;
    an auxiliary electrode;
    a reference electrode;
    means for exposing said working electrode and said auxiliary electrode to a buffered solution of a salt of N,N-diethyl-p-phenylenediamine and said sample;
    means for contacting said reference electrode with the buffered solution of a salt of N,N-diethyl-p-phenylenediamine and said sample;
    means for applying a chosen voltage between said working electrode and said reference electrode, thereby producing a current between said working electrode and said auxiliary electrode; and
    means for measuring the current, whereby free chlorine in the sample is determined therefrom.

16. The apparatus of claim 15, wherein said buffered solution of a salt of N,N-diethyl-p-phenylenediamine and said sample further comprises an iodide salt, whereby the total chlorine in the sample is determined from the measurement of the current.

17. The apparatus of claim 16, wherein the iodide comprises an alkali iodide.

18. The apparatus of claim 17, wherein the alkali iodide comprises potassium iodide.

19. The apparatus of claim 15, wherein the solution is buffered at a pH between 6 and 7.

20. The method of claim 19, wherein the solution is buffered using phosphate salts.

21. The method of claim 19, wherein disodium ethylenediaminetetraacetic acid is added to the solution.

22. The apparatus of claim 15, wherein the auxiliary electrode is selected from the group consisting of gold electrodes and carbon electrodes.

23. The apparatus of claim 15, wherein the salt of N,N-diethyl-p-phenylenediamine is selected from the group consisting of oxalates and sulfates.

24. The apparatus of claim 15, wherein the thiol is selected from the group consisting of alkanethiols, thiols having an alcohol terminus, and fluorinated thiols.

25. The apparatus of claim 24, wherein the alkanethiols comprise alkanethiols having a carbon chain length greater than six carbon atoms.

26. The apparatus of claim 25, wherein the alkanethiol comprises 1-dodecanethiol.

27. The apparatus of claim 24, wherein the thiol having an alcohol terminus comprises 11-mercapto-1-undecanol, and the fluorinated thiols comprise 3,3,4,4,5,5,6,6,7,7,8,8,9,9,10,10,10-heptadecafluoro-1-decanethiol.

28. The apparatus of claim 15, wherein said means for exposing said working electrode, said auxiliary electrode and said reference electrode to a buffered solution of a salt of N,N-diethyl-p-phenylenediamine and said sample comprises a capillary structure defining a volume containing said working electrode, said auxiliary electrode, and the buffered solution of a salt of N,N-diethyl-p-phenylenediamine, said capillary structure having at least one hydrophilic surface and an opening adapted to admit a chosen portion of said sample into the volume when the opening of said capillary structure is contacted with said sample, whereby the buffered solution of a salt of N,N-diethyl-p-phenylenediamine and said sample is formed; and means for contacting said reference electrode with the buffered solution of a salt of N,N-diethyl-p-phenylenediamine and said sample formed in the volume.

* * * * *